United States Patent
Palanker et al.

(10) Patent No.: US 7,556,621 B2
(45) Date of Patent: Jul. 7, 2009

(54) OPTICALLY CONTROLLED MICROFLUIDIC CHIP

(75) Inventors: Daniel V. Palanker, Sunnyvale, CA (US); Harvey A. Fishman, Menlo Park, CA (US)

(73) Assignee: The Board of Trustees of the Leland Stanford Junior University, Palo Alto, CA (US)

( * ) Notice: Subject to any disclaimer, the term of this patent is extended or adjusted under 35 U.S.C. 154(b) by 838 days.

(21) Appl. No.: 11/156,069

(22) Filed: Jun. 17, 2005

(65) Prior Publication Data

US 2006/0116741 A1 Jun. 1, 2006

Related U.S. Application Data

(63) Continuation-in-part of application No. 10/184,210, filed on Jun. 27, 2002, now Pat. No. 7,001,608.

(60) Provisional application No. 60/582,745, filed on Jun. 23, 2004, provisional application No. 60/301,394, filed on Jun. 29, 2001.

(51) Int. Cl.
  *A61M 35/00* (2006.01)
(52) U.S. Cl. ..................................... 604/298
(58) Field of Classification Search ................ 604/89.1, 604/891.1, 294, 22, 93, 257, 285, 289, 300, 604/297, 298
See application file for complete search history.

(56) References Cited

U.S. PATENT DOCUMENTS

| | | | |
|---|---|---|---|
| 5,725,493 A * | 3/1998 | Avery et al. ..................... 604/9 |
| 5,776,748 A | 7/1998 | Singhvi et al. .............. 435/180 |
| 5,900,160 A | 5/1999 | Whitesides et al. ........... 216/41 |
| 6,060,121 A | 5/2000 | Hidber et al. ................ 427/261 |
| 6,180,239 B1 | 1/2001 | Whitesides et al. ....... 428/411.1 |
| 6,196,993 B1 * | 3/2001 | Cohan et al. ............. 604/891.1 |
| 7,017,394 B2 * | 3/2006 | Sullivan .................... 73/64.47 |

OTHER PUBLICATIONS

Marzolin, et al. "Patterning of a Polysiloxane to Silicate Glasses by Microcontact Printing" (1998) Published in Thin Solid Films, 315:9-12.
Quin et al. "Microfabrication, Microstructures and Microsystems" (1998) Published in Microsystem Technology in Chemistry and Life Scciences, vol. 194: 1-20.
Xia et al. "Unconventional Methods for Fabricating and Patterning Nanostructures" (1999) Published in Chem. Rev. 99:1823-1848.

* cited by examiner

*Primary Examiner*—Manuel A Mendez
(74) *Attorney, Agent, or Firm*—Lumen Patent Firm

(57) ABSTRACT

An optically controlled microfluidic chip is provided for administering a fluid to a neuronal site. The chip is made of at least one unit or pixel, each of which constitutively emits fluid in the dark, and reduces emission of fluid in response to light. The individual pixels are capable of being individually controlled, thereby translating a spatial pattern of incident light into a spatial pattern of neuronal stimulation. Each pixel contains a housing, an aperture in the housing, and a reservoir containing fluid that is connected to the aperture. The aperture is designed to allow continuous emission of fluid from the reservoir through the aperture when the pixel is in the dark. Each pixel also includes an optical control, which reduces the emission of fluid from the reservoir through the aperture in response to light.

11 Claims, 3 Drawing Sheets

FIG. 3
A
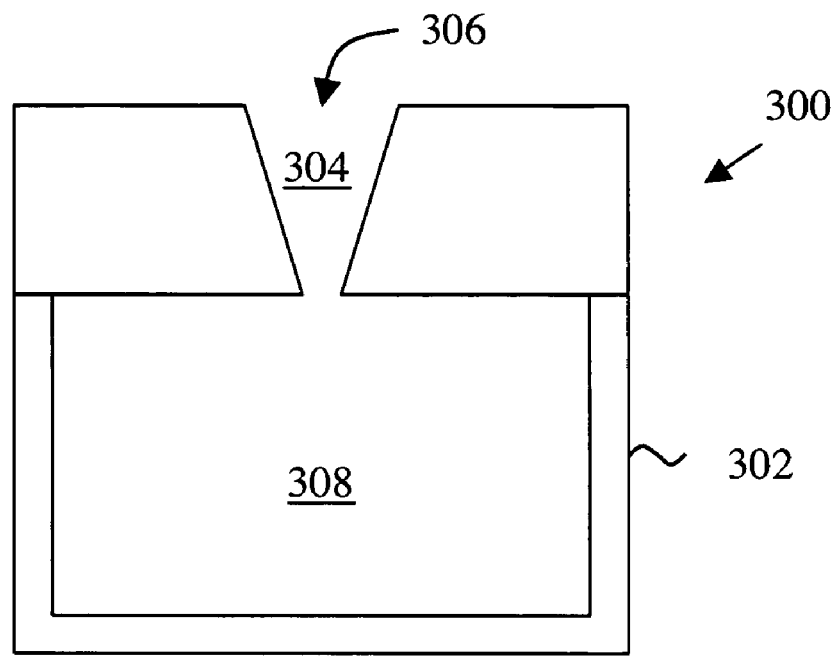
B
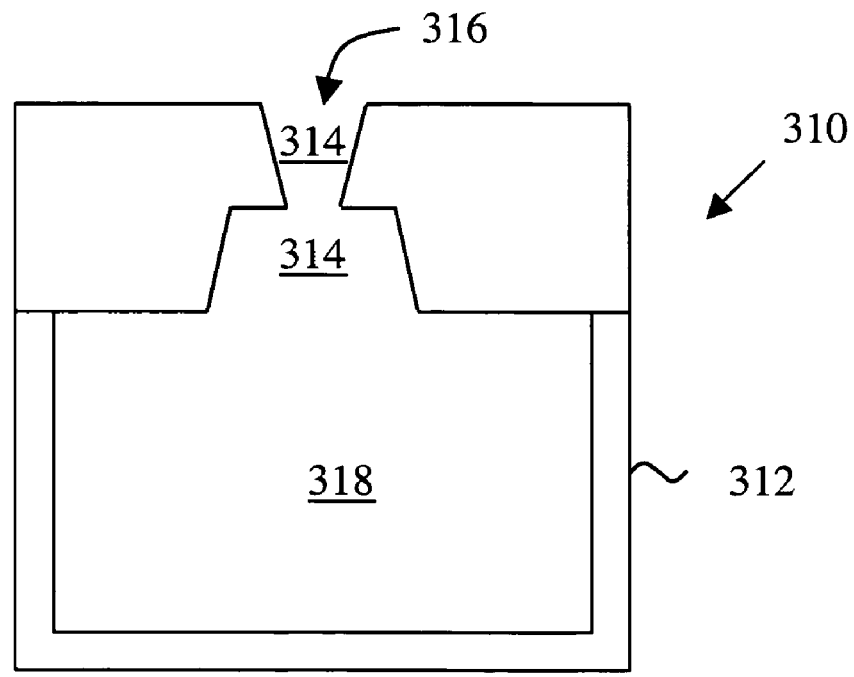

OPTICALLY CONTROLLED MICROFLUIDIC CHIP

CROSS-REFERENCE TO RELATED APPLICATIONS

This application claims priority from U.S. Provisional Patent Application No. 60/582,745, filed Jun. 23, 2004, which is incorporated herein by reference. This application is a continuation-in-part of U.S. patent application Ser. No. 10/184,210, filed Jun. 27, 2002 now U.S. Pat. No. 7,001,608, which claims priority from U.S. Provisional Patent Application No. 60/301,934, filed Jun. 29, 2001, which are incorporated herein by reference.

FIELD OF THE INVENTION

The present invention relates generally to micro-fabricated medical devices. More particularly, the invention relates to microfluidic retinal implants.

BACKGROUND

Age-related macular degeneration (AMD) is one of the most common forms of blindness in people over the age of 65. Currently, there is no effective treatment for most patients with AMD, a disease that often results in permanent damage to photoreceptors, but spares most retinal ganglion cells (RGCs) and second-order neurons, such as bipolar and horizontal cells. Similarly, other diseases such as retinitis pigmentosa (RP) cause visual impairment and blindness due to loss of photoreceptors.

Inherent to the power of the human visual system is the ability to transduce light by individual photoreceptors, thus making it a high-resolution image capture system. Several groups worldwide have carried out clinical experiments to determine if electrically stimulating retinal cells, the optic nerve bundle or cells of the visual cortex with microelectrode arrays can generate phosphenes (i.e. sensations of light) in individuals impaired with AMD. These trials have shown that by electrically stimulating neurons with a microelectrode array, blind individuals can indeed recognize a simple pattern such as a horizontal or vertical line. Although these trials have demonstrated that vision is recoverable in a limited fashion, major challenges remain. Due to the size and difficulties in placement of most available electrodes, imprecise electric field stimulation extending over long distances (several cell-body diameters) is used to depolarize neurons. In addition, such methods often require excessive stimulation, which may be harmful, leading to inflammation of the stimulated region and gliosis.

The limitations in using electrical stimulation warrant the need for other methodologies that do not use electrical stimulation, and more closely mimic physiological stimulation. The natural method of stimulation employs biologically active molecules that at very low concentrations become bound to neuronal receptors resulting in transduced signals, a process known as synaptic transmission. Normally, photoreceptors chronically secrete these biologically active molecules in the dark. When the photoreceptors sense light, they reduce their secretion of these molecules. Downstream neurons respond to this change by changing their polarization and producing electrical signals that are transmitted to other neurons. In response to visual cues, specific neurons are activated to generate an accurate pattern of signals that are sent to the brain for interpretation.

Thus, there is a need in the art for alternative methods and devices that will allow for controlled stimulation of neurons in a more precise and physiologically relevant manner, with constitutive activation in the dark, and reduction in activation in response to light. By allowing for control of one or a few neurons in relation to an external stimulus one can more closely mimic the natural way neuronal cells are stimulated and transmit signals to the brain to permit a visual image or other information.

SUMMARY OF THE INVENTION

The present invention provides an optically controlled microfluidic chip that allows for controlled stimulation of neurons in a more precise and physiologically relevant manner. The chip is made of at least one unit or pixel, each of which constitutively emits fluid in the dark, and reduces emission of fluid in response to light. The individual pixels are capable of being individually controlled, thereby translating a spatial pattern of incident light into a spatial pattern of neuronal stimulation. Each pixel contains a housing, an aperture in the housing, and a reservoir containing fluid that is connected to the aperture. The aperture has a bottom, which is connected to the reservoir, and an exit, through which fluid emits out of the chip. The aperture is designed to allow continuous emission of fluid from the reservoir through the aperture when the pixel is in the dark. Each pixel also includes an optical control, which reduces the emission of fluid from the reservoir through the aperture in response to light.

In a preferred embodiment, the optical control is one or more photodiodes. Upon illumination, the photodiodes produce an electric field between an electrode at the base of the aperture (i.e. the end of the aperture that is connected to the reservoir) and an electrode on the top of the chip that is common to all of the pixels. In a particularly preferred embodiment, the common electrode is transparent. The electric field generated between the electrodes produces an electroosmotic flow through the aperture towards the reservoir, acting against the flow of fluid by diffusion. This results in a reduction of emission of fluid through the exit of the aperture in response to light. Thus, the present invention acts in a much more similar manner to retinal photoreceptors, with constitutive emission of fluid in the dark, and reduced emission of fluid in response to light. In addition, each pixel can be activated independently, providing a spatial pattern of stimulation in response to a spatial pattern of incident light, similar to normal vision.

BRIEF DESCRIPTION OF THE FIGURES

The present invention together with its objectives and advantages will be understood by reading the following detailed description in conjunction with the drawings, in which:

FIG. 3 shows examples of asymmetric apertures according to the present invention.

DETAILED DESCRIPTION OF THE INVENTION

The present invention provides an optically controlled microfluidic chip for controlled release of fluid. The following sections provide details on the components, dimensions, and manufacture of the chip.

Pixels

The optically controlled microfluidic chip is made of one or more units or pixels. Each pixel contains a housing, an aperture in the housing, and a reservoir containing fluid that is connected to the aperture. Each pixel also includes an optical control for limiting emission of fluid through the aperture in response to light. Each pixel may be independently controlled by light, such that a spatial pattern of incident light will translate into a spatially controlled reduction in emission of fluid.

Figure 1:
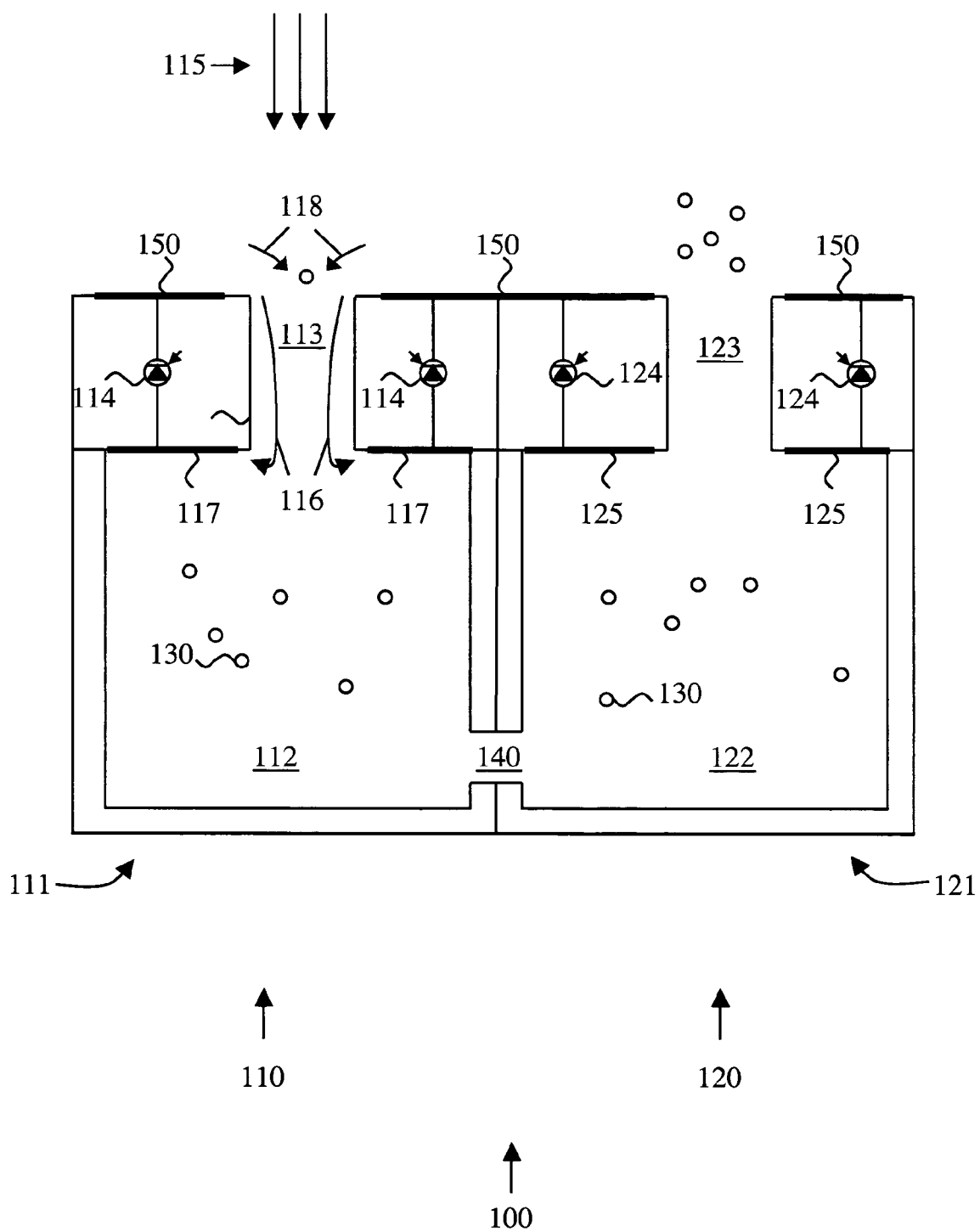
FIG. 1 shows an optically controlled microfluidic chip according to the present invention.

FIG. 1 shows an example of an optically controlled microfluidic chip 100. Optically controlled microfluidic chip 100 has two pixels 110 and 120. Each pixel includes a housing (111 and 121, respectively), a reservoir (112 and 122, respectively), and an aperture (113 and 123, respectively). Reservoirs 112 and 122 contain a fluid, e.g. with neurologically active compounds 130, that can be emitted through apertures 113 and 123. The reservoirs may be connected by a channel 140. The rate of emission of the fluid is controlled by photodiodes 114 and 124. Upon illumination 115 of, for example, pixel 110, photodiodes 114 produce electric fields 116 through aperture 113 between a common transparent electrode 150 and inner electrodes 117. Electric fields 116 produce an electroosmotic flow 118 through aperture 113 into reservoir 112. This electroosmotic flow is against the normal flow of compounds emitted through the aperture, resulting in a reduction in the emission of compounds 130 through aperture 113. In contrast, in this example, pixel 120 does not receive light and shows a normal emission. In other words, photodiode 124 is not activated and therefore no electric field is generated between common electrode 150 and electrodes 125; hence, no electroosmotic flow is produced through aperture 123. Thus, light-activated pixel 110 releases less neurologically active compound 130 than dark pixel 120.

Housing

The housing, generally in the form of a thin film, is usually formed form two layers. The first layer, also called a membrane, contains the aperture. The second layer contains the reservoir. The housing may be rigid or flexible. Rigid chips may be prepared from silicon, silicon nitride, or polymers that are listed below, where rigidity or flexibility relies on the average molecular weight, degree of cross-linking, and the degree of physical interaction between strands, e.g. hydrogen bonding, entwining, etc.

The housing is composed of a biologically compatible, and non-biodegradable material, desirably flexible. For rigid materials, silicon or silicon nitride can be employed. For materials that may be flexible or rigid, depending upon the molecular weight and degree of crosslinking, one may employ organic polymers, such as polysiloxanes (e.g. poly (dimethylsiloxane {PDMS})), polyamides (e.g., nylon), polyesters, polystyrenes, polyacrylates, vinyl polymers (e.g., polyethylene, polytetrafluoroethylene, polypropylene and polyvinyl chloride), polycarbonates, polyurethanes, cellulose acetates, polymethyl methacrylates, ethylene vinyl acetates, polysulfones, nitrocelluloses and mixtures, derivatives and copolymers thereof. The housing may be transparent or semiopaque or opaque.

In order to induce electroosmotic flow (EOF), it is necessary that the walls be charged. Charging of the walls can be achieved in a variety of ways, such as charged monomers that are copolymerized with the primary prepolymer, modification of the prepolymer to introduce random or regularly spaced charged groups, modifying the surface by oxidation using high energy radiation, etc. In addition, the surface may be coated with charged materials, such as proteins. These ways are well established in the art and do not require exemplification here. Alternatively, additives in the medium, such as ions, can be used to provide the charged surface.

Various groups can provide negative or positive charges. Carboxyl, phosphate, phenol, borate, silicic acid, etc. can provide negative charges. Amine, amidine, hydrazine, etc. can provide positive charges. Oxidation of the surface can lead to carboxyl groups or hydroxyl groups that may also play the role of providing a negative charge.

Typically, the desired polymer is one with a low glass transition temperature, $T_g$. The lower the glass transition temperature the higher the flexibility. The glass transition temperature for poly(dimethylsiloxane) is typically in the order of 146° K. Polymers may be functionally modified by changing the structure to increase or decrease their "softness". For instance, combining two polysiloxane chains into a ladder structure, insertion of rigid groups into the structure, or adding bulky side groups will all increase rigidity. The housing may be further modified to present a zeta potential at the fluid interface. In another example, poly(dimethylsiloxane) may be functionally modified by plasma irradiation, which oxidizes the methyl groups present, liberating the carbon atoms and leaving hydroxyl groups in their place. This modification effectively creates a glass-like surface on the polymeric material, with its associated hydroxyl functional groups.

Reservoir

The reservoir contains a fluid and is connected to the aperture. The reservoir contents may be replenished by catheters or feeder tubes connected to an external reservoir. The reservoir may take many shapes, such as tubular, spherical, hemispherical, cubic, combination thereof, or the like, depending upon the manner of fabrication, ease of forming the shape, the desired volume and the size of the unit. The reservoirs will have a capacity of at least about 1 pL, more usually at least about 5 pL and not more than about 500 pL, usually not more than about 100 pL. The chips may have a single or multiple reservoirs containing different fluids. When multiple reservoirs are present in the chips, the contents may enter a central mixing reservoir before discharge of the contents through the aperture.

The fluid in the reservoir may contain bioactive agents or bioagents, such as neuromodulatory agents, which include neurotransmitters, hormones, ions, messenger molecules, nucleic acids, nucleic acid vectors, drugs, etc. Reservoirs may contain any combination of a bioactive agent, and a buffer. The bioactive agent present in a reservoir may include any combination of neuromodulatory agents, for example, neurotransmitters, hormones, ions, messenger molecules, or liposomes. Neuromodulatory agents include, for example, amino acids, such as glutamate, aspartate, and glycine; N-methyl-D-aspartate (NMDA), α-amino-3-hydroxy-5-methyl-4-isoxalonepropionic acid (AMPA), quisqualate, kainate, and anlogs thereof; gluaminergic and glycinergic agents; cholinergic agents, such as acetylcholine, suberyldicholine, analogs thereof, etc.; catecholamines or adrenergic agents, e.g. dopamine, L-dopamine, norepinephrine, epinephrine, etc., histamine serotonin and serotonergic agents; γ-aminobutyric acid and GABA-ergic agents; taurine, octopamine, nucleotides e.g., adenosine triphosphate, adenosine diphosphate, guanosine triphosphate, or guanosine diphosphate, cyclic nucleotides, messenger agents, such as peptide hormones, e.g. enkephalins, dynorphin, endorphin, adrenocortiocotropic hormone ACTH, vasoactive intestinal peptide (VIP), etc; steroid hormones and active ions, e.g. $Ca^{+2}$, $Zn^{+2}$, $K^+$, etc.

Importantly, neuromodulatory agents include all agents that affect receptors present on neurons. These include agents that modify the receptors, including, and not limited to, glutamate receptors, NMDA-receptors, AMPA-receptors, glycine receptors, dopamine receptors, acetylcholine receptors, and acetylcholine receptors. The bioactive agent may be in combination with a buffer, for example, phosphate buffered saline, HEPES-buffered saline, MOPS-buffered saline, Dulbecco's Modified Eagle's medium, or bicarbonate-buffered saline. Neuronal cells that can be affected include unipolar cells, bipolar cells, ganglions, pyramidal cells, glial cells, astrocytes, motor, Purkinje cell, horizontal cell of Cajal, etc.

Included among bioagents are channel forming molecules, such as α-hemolysin, gramicidin, alamethicin, etc., sugars, dyes, sources of cellular energy, etc. The bioagents may be present as micelles, liposomes, biological membrane preparations containing ion channels and/or receptors, etc., where the bioagents containing membrane may fuse with the cellular membrane.

Aperture

The optically controlled microfluidic chip has an aperture that permits constitutive emission of fluid from the reservoir in the dark. The aperture may have an opening flush with the chip surface or recessed, so as to be flush with the bottom of a well. Electrodes may be placed in proximity to the aperture to regulate the flow of fluid. In one embodiment, recording electrodes may be placed in or near the aperture, permitting simultaneous electrical recording and chemical stimulation of neurons.

Figure 2:
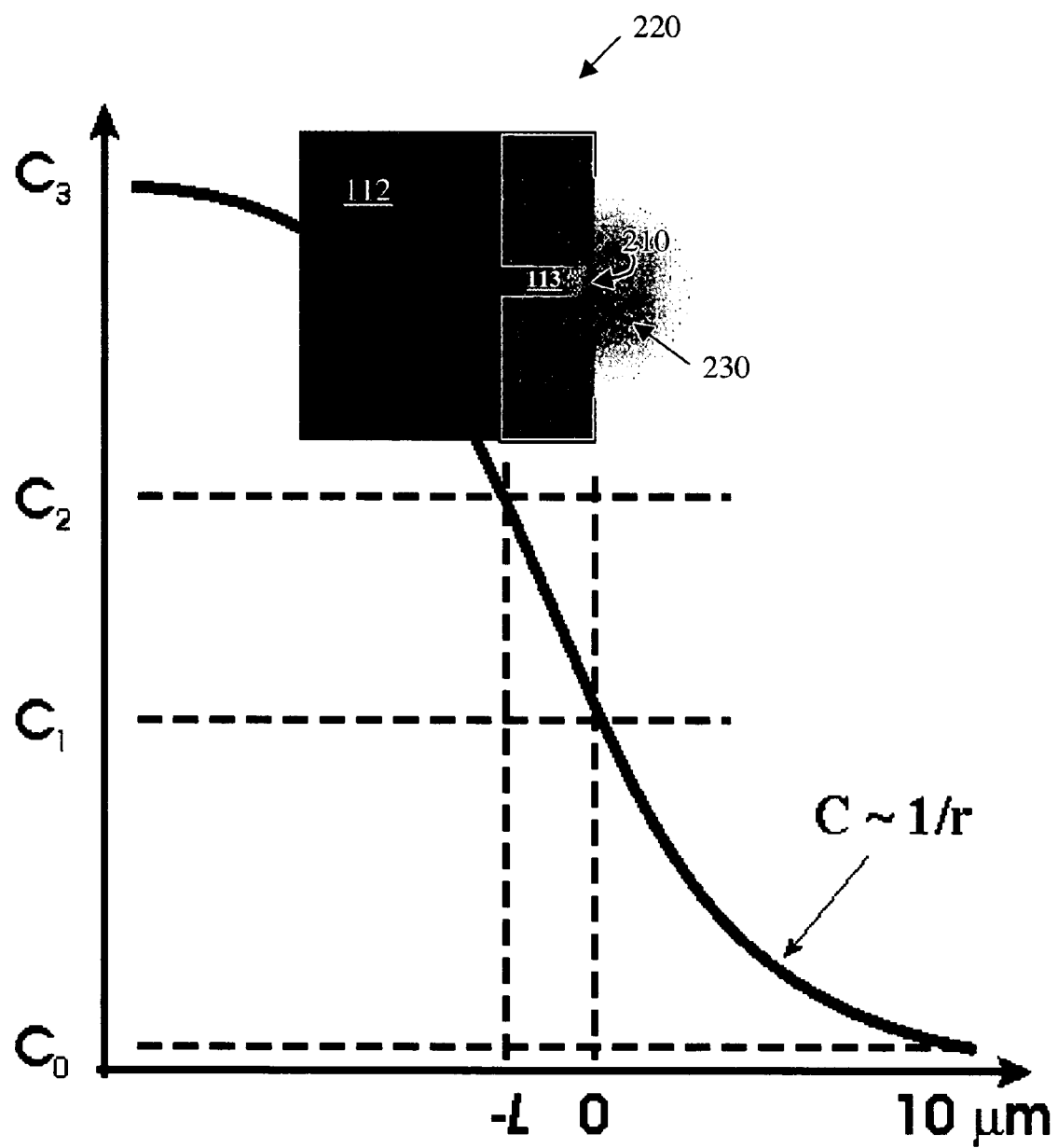
FIG. 2 shows a relationship between distance from the exit of the aperture and bioagent concentration according to the present invention.

FIG. 2 shows a relationship between distance from exit 210 of aperture 113 of pixel 220 and bioagent 230 concentration C according to the present invention. In a steady state the concentration C of a bioagent at distance r from exit 210 of aperture 113 with radius $r_0$ is: $C = C_1 \cdot r_0/r$, where $C_1$ is the concentration of bioagent at exit 210. Assuming that the concentration of bioagent required for cellular stimulation $C_1 = 1$ mM, and that the concentration 10 μm away from the aperture should be below toxic level $C_0 = 10$ μM, we obtain that the radius of the aperture should be $r_0 = 0.11$ μm. The concentration of bioagent inside reservoir 112 $C_2 = C_1(1+L/r_0)$, where L is the depth of the aperture or thickness of the membrane that contains the aperture. For L=1 μm, $C_2 = 11$ mM. A time constant τ associated with diffusion coefficient D depends on distance r from exit 210 as $\tau = r^2/D$. For example, for small proteins, such as glutamate, $D = 10^{-6}$ cm$^2$/s, thus the concentration within 1 μm from the aperture can change during τ=10 ms. This means that if a cell is located within 1 μm from the aperture, it can follow the changes of emission rate at frequencies of about 100 Hz. However, if the cell is located 10 μm away from the aperture, the diffusion time will be 1 s, corresponding to a frequency of 1 Hz, which is much slower than normal vision. Critical dependence of the stimulation rate on distance between the cell and the aperture necessitates special techniques ensuring their close proximity. For example, a micropattern may be provided on the chip outer surface proximal to a neuronal site comprising a viable neuron(s). The micropattern may direct growth of a cell process towards the chip aperture.

Diffusion drift velocity of molecules at exit 210 $\upsilon = D \cdot \text{grad}(C)/C = D/r_0 = 1$ mm/s in our case. Electroosmotic flow at this rate can be achieved with electric potential U=0.7 V applied across an aperture of 1 μm depth. Electric impedance of the aperture in physiological medium is about 5 MOhm, corresponding to the electric power $P = U^2/R = 0.1$ μW per aperture. With a pixel size of 20 μm, the total number of pixels on a 3 mm chip is 18,000, and total power will be 1.8 mW. This power dissipation corresponds to a temperature rise of 0.26° C. at the chip surface, which is well below the acceptable limit of 1° C. To prevent irreversible electrochemical reactions the electric current should be bi-phasic and charge-balanced. Application of electric pulses of opposite polarities will generate electro-osmotic flow in opposite directions, which on average will cancel the effect of the flow at all. To avoid this, the aperture in the present invention may be asymmetric. Two asymmetric apertures according to the present invention are shown in FIG. 3A and FIG. 3B. In FIG. 3A, pixel 300 with housing 302 contains an aperture 304 that is wider at exit 306 than where it is connected to reservoir 308. In FIG. 3B, pixel 310 with housing 312 contains an aperture 314 that starts out wide at exit 316, narrows, and then expands again at the entrance to reservoir 318. FIG. 3B, in particular, has lower hydrodynamic impedance in the direction towards the reservoir, thus resulting in faster flow in that direction than in the opposite one, when the bi-phasic pulses are applied.

Optical Control

The optical control reduces emission of fluid from the reservoir through the exit in the aperture in response to light. In a preferred embodiment, the optical control is one or more photodiodes. Upon illumination, the photodiodes conduct current and thus produce an electric field between electrodes, resulting in electroosmotic flow from the exit to the bottom of the aperture. Electrodes and connecting wires are formed by any conductive material, for example, metals or metal oxides, such as platinum, palladium, iridium, iridium oxide, titanium nitride, silver, silver chloride, chromium, tin, indium, indium tin oxide, zinc oxide, gold, or aluminum. The chip may contain a single electrode pair or a multiplicity of electrodes or electrode pairs.

Photodiodes can be plated at any convenient sites to provide for an electrical source for the electroosmotic flow, particularly, where the transparent nature of the material allows for light, e.g. from the eye, to irradiate the photodiodes and create a current. The photodiodes may be formed at the ports on opposite sides of the aperture or another site.

Dimensions

Individual pixels will generally have a surface area in the range of about 2 to 50 μm$^2$, more usually about 5 to 25 μm$^2$, where larger or smaller surface areas may be employed in particular environments. For retinal use, the surface area will usually not exceed 15 μm$^2$, more usually not exceed 10 μm$^2$ and will generally have a surface area of at least about 2 μm$^2$. Chips with multiple pixels will generally have a surface area in the range of about 10 to 500 μm$^2$, more usually not more than about 200 μm$^2$. Apertures will generally be spaced apart at least about 2 μm, more usually at least about 5 μm and generally not more than about 50 μm, more usually not more than about 25 μm. The larger the area, the more desirable it is to have the chip shaped to accommodate the particular surface to provide the desired interaction and to localize the agent that is emitted from the chip. The chips may have a generally round, elliptical, rectangular, tubular or other form, where the edges may be rounded. Aperture diameters will generally be between 0.01 to 10 μm, more usually 0.05 to 2 μm.

The layers that form the chip will generally have a thickness in the range of at least about 1 μm and not more than about 2 mm, usually not less than 10 μm and not more than about 0.2 mm, where when an adhesive layer is used, it will have a thickness in the lower part of the range. The layer thickness provides mechanical stability and ease of handling of the chip in implanting the chip, particularly for implanting in the epiretinal or subretinal region, and ease of retrieving the chip when the contents are spent or the chip is no longer required.

The implant will be shaped to fit in the region in which it is to be placed. For example, for the retina, the chip must be small enough to fit comfortably against the retina in the retinal region, epiretinal or subretinal. While larger and smaller chips may be constructed, generally the thickness of the chip will be in the range of about 20-500 μm, more usually from about 50 to 300 μm.

Fabrication

Microfabrication is readily employed for construction of the chip. Standard silicon process techniques are readily adapted for producing the subject chips. Using low-pressure chemical vapor deposition, silicon nitride is grown on the surface of orientation silicon wafers. A combination of lithography to define the structures in a photosensitive polymer is followed by plasma etching to pattern the structures in the silicon nitride to create apertures on one side of the wafer and an etchant masking layer on the other side. An anisotropic etchant, such as tetramethylammonium hydroxide (TMAH) is used to remove the silicon along the crystal plane, leaving the silicon nitride unaffected. This results in a via opening (a connecting passageway) beneath the aperture, exposing the silicon nitride membrane and completing the processing.

The conduit or via opens into a microfluidic channel that serves as a reservoir for bioagents. The microfluidic channel is made from a standard PDMS stamp and sealed to the wafer. Such a microfluidic channel can be readily sealed to the wafer with a stable seal. The PDMS stamp having a channel is bonded to a silicon nitride surface after acid cleaning (e.g. HCl) and plasma treating, forming an irreversible bond. The resulting channel can serve as a general-purpose buffer reservoir for dealing with waste products and for delivering bioagents. Apertures may be formed smaller than the length scale of a neuron to insure that only a single cell is stimulated.

Methods for microfabrication or nanofabrication are described in U.S. Pat. Nos. 5,776,748, 5,900,160; 6,060,121; and 6,180,239; and such articles as: "Patterning of a Polysiloxane Precursor to Silicate Glasses by Microcontact Printing," Marzolin, et al., Thin Solid Films 1998, 315, 9-12; "Microfabrication, Microstructures and Microsystems," Qin, et al., In: Microsystem Technology in Chemistry and Life Sciences, vol. 194, Manz, A and Becker, H eds., Springer-Velag, Berlin, 1998, 1-20; and "Unconventional Methods for Fabricating and Patterning Nanostructures," Xia, et al., Chem Rev 99:1823-48 (1999). All patents both supra and infra, are hereby incorporated by reference in their entirety. Electrodes and other elements may be formed using techniques known in the art, e.g., sputtering and controlled vapor deposition methods followed by chemical etching, and the like.

Methods of Implanting the Chip

The subject chips can be inserted intraocularly adjacent to the retina, subretinally or epiretinally. After anesthetizing the area, a standard 3-port pars plana vitrectomy can be employed, with epiretinal implants inserted through the sclerectomy. For subretinal implants, a subretinal bleb is formed in the macular area, a retinotomy created and the implant inserted into the subretinal space. At other site, similar protocols can be employed for insertion of the implant in association with the neuronal structure.

All references referred to in the text are incorporated herein by reference as if fully set forth herein. The relevant portions associated with this document will be evident to those of skill in the art. Any discrepancies between this application and such reference will be resolved in favor of the view set forth in this application.

What is claimed is:

1. An optically controlled microfluidic chip comprising:
   (a) a reservoir containing a fluid;
   (b) an aperture, wherein said fluid is capable of emitting from said reservoir through said aperture; and
   (c) an optical control for sensing light and regulating the emission of said fluid through said aperture based on an amount of light received,
   wherein said fluid is emitted from said reservoir through said aperture by diffusion when said optical control is not illuminated, and wherein said optical control reduces the emission of said fluid in response to said received light.

2. The chip as set forth in claim 1, wherein said optical control comprises one or more photodiodes.

3. The chip as set forth in claim 1, wherein said optical control generates a biphasic and charge-balanced electric current.

4. The chip as set forth in claim 1, wherein said aperture is asymmetric.

5. The chip as set forth in claim 1, wherein said aperture has a diameter in the range of about 0.01-10 μm.

6. The chip as set forth in claim 1, wherein said aperture has a diameter in the range of about 0.05-2 μm.

7. The chip as set forth in claim 1, wherein said optical control produces an electroosmotic flow through said aperture towards said reservoir to reduce the emission of said fluid, and wherein said electroosmotic flow is produced when said optical control is illuminated.

8. The chip as set forth in claim 7, wherein said electroosmotic flow is in the opposite direction as the flow by diffusion of said fluid.

9. The chip as set forth in claim 1, wherein said fluid comprises a neurologically active compound to stimulate one or more neurons.

10. The chip as set forth in claim 1, wherein said chip is implantable adjacent to a retina.

11. An optically controlled microfluidic chip for translating a spatial pattern of incident light into a pattern of neuronal stimulation, said chip comprising a plurality of pixels, wherein each of said pixels comprises:
   (a) a reservoir containing a fluid, wherein said fluid comprises a neurologically active compound for stimulating one or more neurons;
   (b) an aperture for each of said pixels, wherein said fluid is capable of emitting from said reservoir through said aperture; and
   (c) an optical control for each of said pixels, wherein said optical control regulates the flow of said fluid through said aperture of the same of said pixels based on an amount of light received,
   wherein said fluid is emitted from said reservoir through said aperture by diffusion when the same of said pixel is not illuminated, wherein said optical control reduces the emission of said fluid in response to said received light, and
   wherein said optical control of said pixels are independently controlled by said spatial pattern of incident light.

* * * * *